(12) United States Patent
Kho et al.

(10) Patent No.: US 9,833,218 B2
(45) Date of Patent: Dec. 5, 2017

(54) APPARATUS FOR PROCESSING ULTRASONIC IMAGE AND METHOD THEREOF

(71) Applicant: SAMSUNG ELECTRONICS CO., LTD., Suwon-si (KR)

(72) Inventors: Young Ihn Kho, Seoul (KR); Sun Kwon Kim, Suwon-si (KR); Sung Chan Park, Suwon-si (KR); Hee Sae Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 44 days.

(21) Appl. No.: 14/283,894

(22) Filed: May 21, 2014

(65) Prior Publication Data

US 2014/0350403 A1 Nov. 27, 2014

(30) Foreign Application Priority Data

May 21, 2013 (KR) ........................ 10-2013-0056982

(51) Int. Cl.
*A61B 8/00* (2006.01)
*A61B 8/08* (2006.01)

(52) U.S. Cl.
CPC ............ *A61B 8/464* (2013.01); *A61B 8/4494* (2013.01); *A61B 8/483* (2013.01); *A61B 8/5269* (2013.01); *A61B 8/4405* (2013.01); *A61B 8/56* (2013.01); *A61B 8/565* (2013.01)

(58) Field of Classification Search
None
See application file for complete search history.

(56) References Cited

U.S. PATENT DOCUMENTS

| 6,132,379 A * | 10/2000 | Patacsil .................... A61B 8/06 600/459 |
| 2002/0045822 A1* | 4/2002 | Powers ..................... A61B 8/06 600/443 |
| 2005/0283072 A1* | 12/2005 | Qin ....................... A61B 8/0875 600/437 |
| 2009/0208080 A1 | 8/2009 | Grau et al. |
| 2011/0028846 A1* | 2/2011 | Tsao ........................ G01S 7/5208 600/459 |
| 2013/0030296 A1* | 1/2013 | Miyaki ............... G01S 7/52033 600/442 |

FOREIGN PATENT DOCUMENTS

| JP | 2005-300222 A | 10/2005 |
| JP | 2006-10508 A | 1/2006 |
| JP | 2007-301218 A | 11/2007 |
| JP | 2012-122870 A | 6/2012 |

OTHER PUBLICATIONS

Makris, Nicholas C., Bertsatos, Ioannis, Resolving Lambertian Surface Orientation from Fluctuating Radiance, Sep. 2011, Journal of Acoustistical Society of America 130 (3), 1222-1231.*

* cited by examiner

*Primary Examiner* — Tse Chen
*Assistant Examiner* — Joanne Hoffman
(74) *Attorney, Agent, or Firm* — Sughrue Mion, PLLC

(57) ABSTRACT

An ultrasonic imaging method includes emitting ultrasonic pulses in different directions and acquiring ultrasonic echo signals from an object, calculating an attenuation rate of the ultrasonic echo signals, correcting the acquired ultrasonic echo signals based on the attenuation rate, and outputting the corrected ultrasonic echo signals as an ultrasonic image.

14 Claims, 11 Drawing Sheets

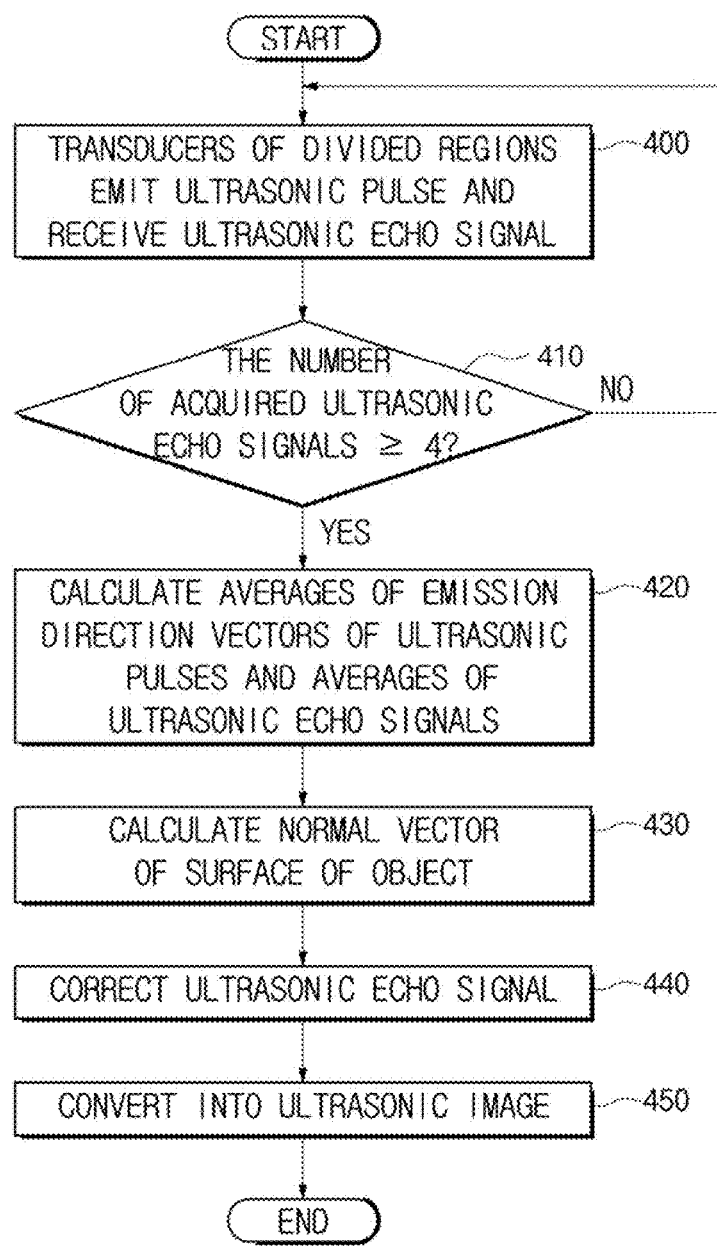

APPARATUS FOR PROCESSING ULTRASONIC IMAGE AND METHOD THEREOF

CROSS-REFERENCE TO RELATED APPLICATION

This application claims priority from Korean Patent Application No. 10-2013-0056982, filed on May 21, 2013 in the Korean Intellectual Property Office, the disclosure of which is incorporated herein by reference in its entirety.

BACKGROUND

1. Field

Apparatuses and methods consistent with exemplary embodiments relate to an apparatus for processing an ultrasonic image which generates an image using ultrasonic signals and a method thereof.

2. Description of the Related Art

An ultrasonic diagnostic apparatus emits ultrasonic waves toward a target region of an object from the surface of the object and generates an image of the target region such as a soft tissue tomogram or a blood stream image using reflected ultrasonic signals, i.e., ultrasonic echo signals.

The ultrasonic diagnostic apparatus is widely used for heart diagnosis, breast diagnosis, celiac diagnosis, urinary diagnosis, and obstetric diagnosis.

An ultrasonic diagnostic apparatus includes a main body, an ultrasonic transceiver that transmits and receives ultrasonic waves, a control panel provided with a variety of switches and keys used to input commands for manipulation of the ultrasonic diagnostic apparatus, and a display that displays the result of ultrasonic diagnosis using an image.

A process of performing ultrasonic diagnosis using the ultrasonic diagnostic apparatus is as follows. First, a medical professional such as a radiologist or a doctor performs ultrasonic imaging by moving the ultrasonic transceiver in a state of contacting the surface of the body of the object with one hand and manipulating the control panel with the other hand. An ultrasonic image acquired during the ultrasonic imaging is displayed on the display in real time, so that the medical professional may examine the images and provide diagnosis of the object.

Tissues constituting the human body have different reflectivity and absorption with respect to ultrasonic signals. In an ultrasonic diagnostic imaging, the composition of materials constituting the human body is revealed by analyzing the intensity of ultrasonic waves reflected from the human body. That is, when ultrasonic waves are emitted to the same medium, reflected ultrasonic waves should have the same intensity. However, the intensity of ultrasonic waves actually reflected by an interface between media varies according to respective proceeding directions of the ultrasonic waves and angles of incidence of the ultrasonic waves at the interface between media, and thus characteristics of the media may be distorted.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an apparatus for processing an ultrasonic image capable of correcting intensity of actual reflected ultrasonic waves by emitting a plurality of ultrasonic pulses in different directions using spatial division and a method thereof.

In accordance with an aspect of an exemplary embodiment, a method of processing an ultrasonic image includes emitting a plurality of ultrasonic pulses in different directions and acquiring a plurality of ultrasonic echo signals from an object, calculating an attenuation rate of the ultrasonic echo signals, correcting the acquired ultrasonic echo signals based on the attenuation rate, and outputting the corrected ultrasonic echo signals as an ultrasonic image.

In accordance with an aspect of an exemplary embodiment, an ultrasonic image processing apparatus includes an ultrasonic probe emitting a plurality of ultrasonic pulses in different directions and receiving a plurality of ultrasonic echo signals from an object, an attenuation rate obtainer to calculate an attenuation rate of the ultrasonic echo signals, a corrector to correct the acquired ultrasonic echo signals based on the attenuation rate, a beamformer to covert the corrected ultrasonic echo signals into ultrasonic image signals, and a display to output the converted ultrasonic image signals as an image.

BRIEF DESCRIPTION OF THE DRAWINGS

The above and/or other aspects will be more apparent by describing certain exemplary embodiments with reference to the accompanying drawings, in which:

FIG. 10 is a flowchart illustrating a method of processing an ultrasonic image when four or more ultrasonic echo signals are acquired.

DETAILED DESCRIPTION

Figure 1:
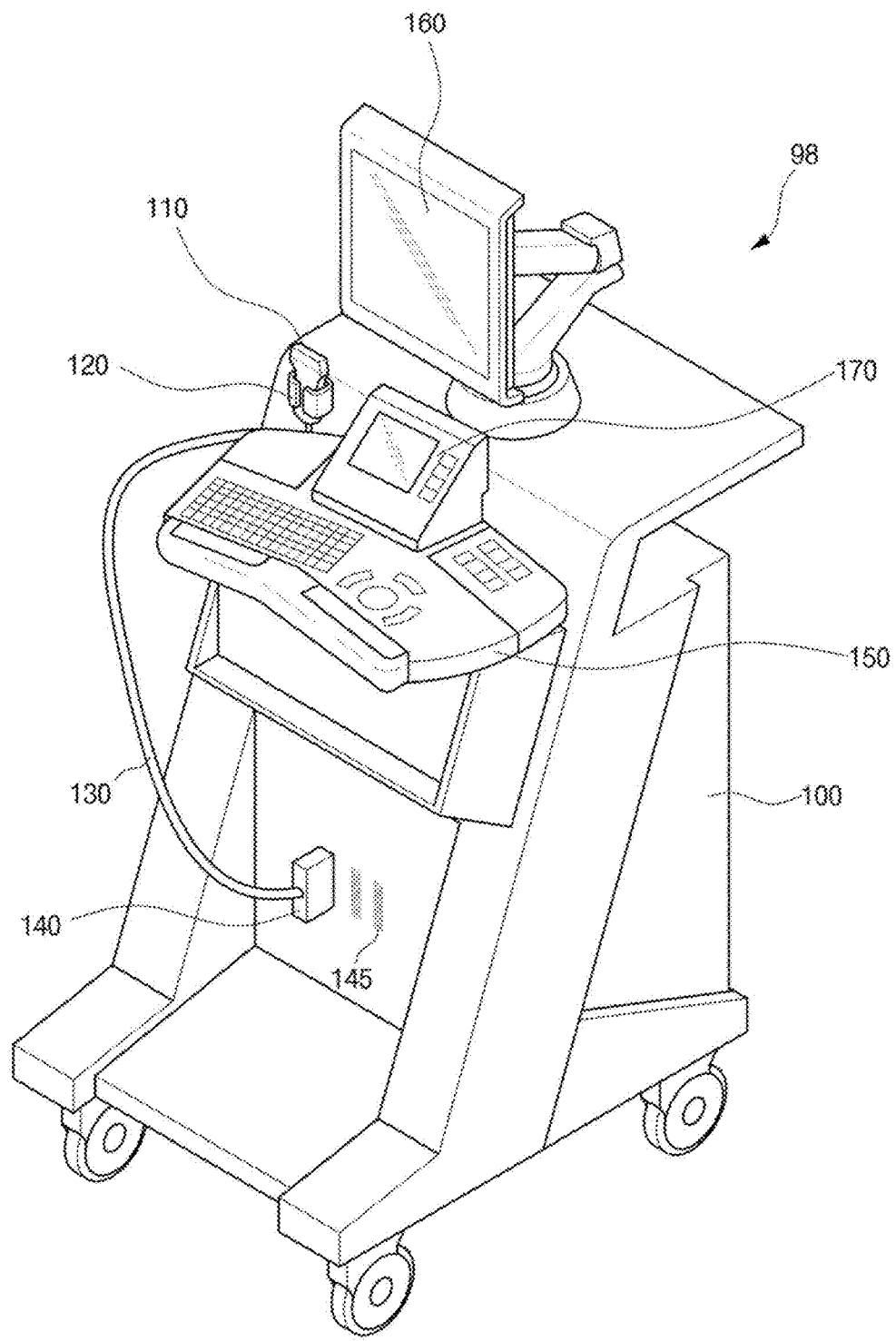
FIG. 1 is a perspective view illustrating an apparatus for processing an ultrasonic image according to an exemplary embodiment.

Exemplary embodiments are described in greater detail with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a perspective view illustrating an apparatus for processing an ultrasonic image according to an exemplary embodiment. As illustrated in FIG. 1, the ultrasonic image processing apparatus 98 includes a main body 100, an ultrasonic transceiver 110 that is an ultrasonic probe, an input unit 150, a main display 160, and a sub-display 170.

More than one female connector 145 may be provided at one side of the main body 100. A male connector 140 connected to a cable 130 may be physically coupled to the female connector 145.

A plurality of casters (not shown) may be provided at the bottom of the main body 100 to provide mobility of the ultrasonic image processing apparatus. The plurality of casters may fix the ultrasound image processing apparatus at a particular place, or may allow the ultrasound image processing apparatus to be moved in a particular direction.

The ultrasonic probe 110 that contacts the surface of the body of an object may transmit and receive ultrasonic waves. Particularly, the ultrasonic probe 110 may emit a transmission signal received from the main body 100, i.e., an ultrasonic signal, into the body of the object and receive an ultrasonic echo signal reflected from a particular region of the object inside the human body so as to transmit the ultrasonic echo signal to the main body 100. One end of the cable 130 may be connected to the ultrasonic probe 110, and the other end of the cable 130 may be connected to the male connector 140. The male connector 140 connected to the other end of the cable 130 may be physically coupled to the female connector 145 of the main body 100.

The input unit 150 may receive an instruction related to operation of an ultrasound image generating apparatus. For example, the input unit 150 may receive an instruction to select a mode, such as an A-mode (Amplitude mode), B-mode (Brightness mode), and M-mode (Motion mode), or an instruction to initiate ultrasonic diagnosis. The instructions input through the input unit 150 may be transmitted to the main body 100 via a wireless or wired communication network.

For example, the input unit 150 may include at least one of a touchpad, a keyboard, a foot switch, and a foot pedal. The keyboard may be a hardware element located at an upper portion of the main body 100. The keyboard may include at least one of a switch, a key, a joystick, and a trackball. In another example, the keyboard may also be a software element, such as a graphical user interface. In this case, the keyboard may be displayed via at least one of the sub-display 170 and the main display 160. The foot switch or the foot pedal may be provided at a lower position of the main body 100, and a manipulator may control operation of the ultrasound image processing apparatus using the foot pedal.

A probe holder 120 in which the ultrasonic probe 110 is placed may be provided near the input unit 150. More than one ultrasonic probe holder 120 may be provided. The medical professional may place the ultrasonic probe 110 in the ultrasonic probe holder 120 for storage when the ultrasonic image processing apparatus is not in use.

Figure 4:
FIG. 4 is a three-dimensional (3D) ultrasonic image of a fetus output by a 3D ultrasonic imaging device.

The sub-display 170 may be provided at the main body 100. FIG. 4 illustrates the case in which the sub-display 170 is located above the input unit 150. The sub-display 170 may display applications related to operation of the ultrasound image processing apparatus. For example, the sub-display 170 may display, e.g., a menu or guide map for performing ultrasonic diagnosis. The sub-display 170 may, for example, take the form of a Cathode Ray Tube (CRT) or a Liquid Crystal Display (LCD).

The main display 160 may be provided at the main body 100. FIG. 4 illustrates the case in which the main display 160 is located above the sub-display 170. The main display 160 may display an ultrasonic image acquired during the ultrasonic diagnosis. The main display 160 may be a CRT or LCD, similar to the sub-display 170. Although FIG. 1 illustrates the main display 160 as being coupled to the main body 100, the main display 160 may be separable from the main body 100.

Although FIG. 1 illustrates that the ultrasonic image processing apparatus includes both the main display 160 and the sub-display 170, the sub-display 170 might not be used. In this case, applications or a menu displayed on the sub-display 170 may be displayed on the main display 160.

Figure 2:
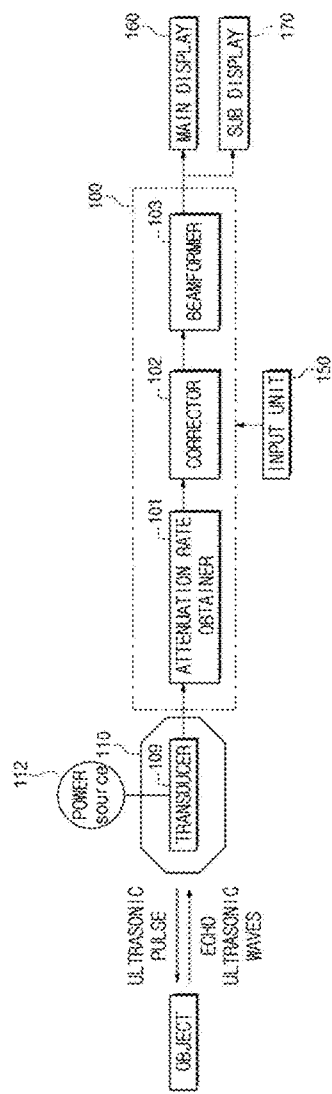
FIG. 2 is a control block diagram illustrating an apparatus for processing an ultrasonic image according to an exemplary embodiment.

FIG. 2 is a control block diagram illustrating an ultrasonic image processing apparatus according to an exemplary embodiment.

A method of processing an ultrasonic image according to the present exemplary embodiment will be briefly described with reference to the control block diagram. The ultrasonic probe 110 receives a plurality of echo ultrasonic waves from an object and converts the echo ultrasonic waves into ultrasonic echo signals that are electronic signals. An attenuation rate obtainer 101 calculates an attenuation rate indicating the amount of loss from the ultrasonic echo signals actually reflected from the object based on the acquired ultrasonic echo signals. A corrector 102 corrects the ultrasonic echo signals based on the calculated attenuation rate, and a beamformer 103 converts the corrected ultrasonic echo signals into ultrasonic image signals. A display 160 displays the converted ultrasonic image signals on a screen to acquire an image from which distortion caused when a virtual light source is located on the path of the ultrasonic probe 110 is removed.

Hereinafter, cause and result of the distortion when the object is illuminated by a virtual light source located on the path of the ultrasonic probe 110 will be described with reference to FIGS. 3 and 4.

Ultrasonic diagnosis using an ultrasonic image is performed by use of the pulse-echo principle. A transducer 109, as an element of the ultrasonic probe 110, may generate ultrasonic pulses and includes a plurality of transducers 111. Each of the generated ultrasonic pulses proceeds at a constant speed until the ultrasonic pulse encounters a reflective surface inside the body of the object. When the ultrasonic pulse encounters the reflective surface, a portion of the ultrasonic pulse is reflected therefrom and returns toward an ultrasonic source, and the other portion of the ultrasonic pulse continuously proceeds in the proceeding direction. The reflective surface is formed at an interface between two media having different densities, i.e., an interface between two different tissues. The reflectivity is proportional to a density difference between the two media. Thus, the composition of substances constituting the human body may be revealed via analysis of the reflected ultrasonic waves. The analysis results are used to examine the tissues of the human body and to generate an image for utilization during diagnosis.

Figure 3:
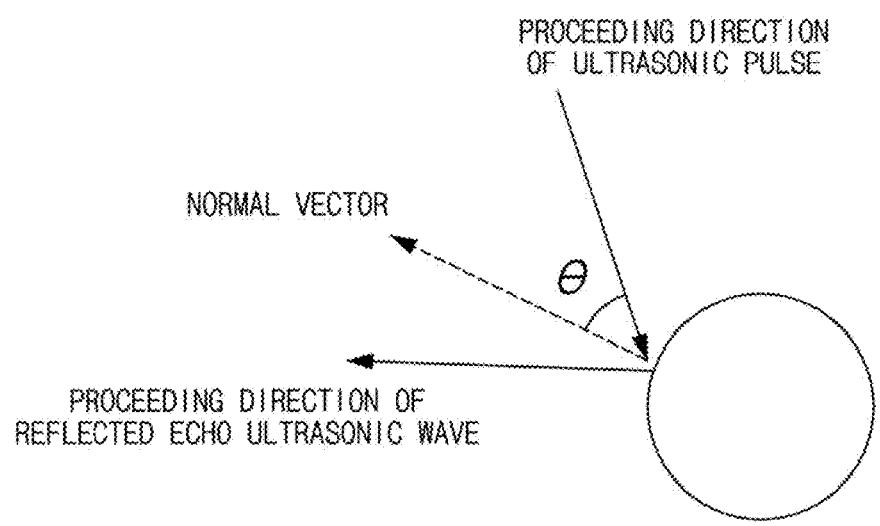
FIG. 3 is a diagram for describing reflectivity according to a reflective surface and a proceeding direction of a pulse.

FIG. 3 is a diagram for describing reflectivity according to a reflective surface and a proceeding direction of a pulse. Reflectivity at the reflective surface is obtained as an intrinsic value according to the density difference between two media. In this regard, the intrinsic value according to the density difference between two media is referred to as sound impedance. Thus, when the same ultrasonic waves are emitted to objects formed of the same medium, reflected echo ultrasonic waves have the same intensity.

However, the intensity of the echo ultrasonic waves reflected from the same medium may vary. This is because, the amount of the reflected ultrasonic echo signals may be influenced by an angle between an emission direction of the ultrasonic pulse and the reflective surface of the object. That is, as the reflective surface of the object is more perpendicular to the emission direction of the ultrasonic pulse, the amount of the ultrasonic echo signals returning to the ultrasonic source increases. On the other hand, as an angle between the normal vector with respect to the reflective surface of the object and the emission direction of the ultrasonic pulse increases, the amount of the ultrasonic echo signals returning to the ultrasonic source decreases.

FIG. 4 is a three-dimensional (3D) ultrasonic image of a fetus output by a 3D ultrasonic imaging device. As described above, since intensities of ultrasonic waves reflected from the same medium vary, distortion is caused in the ultrasonic image due to such intensity differences. Such phenomenon is more serious particularly in a three-dimensional (3D) ultrasonic system. In the 3D ultrasonic system, a light source emitting light in a predetermined direction is set based on volume data, and change of a 3D image is observed while emitting light in different directions. In this case, distortion caused by a virtual light source located on the path of the ultrasonic probe 110, i.e., an ultrasonic source, separately from a light source to observe a 3D image, is obtained.

Referring to FIG. 4, an effect as if the fetus would be illuminated at the front thereof is obtained although lighting is not considered during rendering. For example, shadows of the forehead, portions near the nose, and portions near the eyes are differently expressed in the image of the fetus, although they are parts of the skin formed of the same medium. This indicates that data is acquired as if the fetus would be illuminated by a light source located on the path of the ultrasonic probe 110. Such phenomenon does not cause problems while performing a basic rendering process. However, a serious problem may be caused when a virtual light source is introduced and the external appearance of the object is observed while changing the emission direction thereof. Distortion is caused due to the effect as if the light source would be located at the position of the ultrasonic probe 110, and thus an unnatural image is acquired. Accordingly, an ultrasonic image with high realism may be acquired by removing the effect as if the light source would be located at the position of the ultrasonic probe 110.

Hereinafter, an ultrasonic image processing apparatus and a method of operating the same to remove distortion from an ultrasonic image will be described in detail.

Referring back to FIG. 2, the ultrasonic probe 110 includes a plurality of transducers 111 that generate ultrasonic pulses in accordance with supplied alternating current (AC) power from a power source, emit the generated ultrasonic pulses, receive reflected ultrasonic pulses from a target region of an object, and convert the received echo ultrasonic waves into electrical ultrasonic echo signals. Here, the power source 112 may be an external power supply or an internal capacitor of the ultrasonic image processing apparatus.

Various transducers 111 such as a magnetostrictive ultrasonic transducer using a magnetostrictive effect of a magnetic material, a piezoelectric ultrasonic transducer using a piezoelectric effect of a piezoelectric material, a capacitive micromachined ultrasonic transducer (cMUT), which transmits and receives ultrasonic waves using vibration of hundreds or several thousands of micromachined thin films, may be used.

When alternating current is supplied to the transducers 111 from the power source 112, piezoelectric vibrators or thin films of the transducers 111 vibrate, thereby generating ultrasonic pulses. The generated ultrasonic pulses are emitted to the object, for example, a human body. The emitted ultrasonic pulse is reflected by at least one of the target regions located at various depths in the object. The transducers 111 receive echo ultrasonic waves reflected from the target region and convert the received echo ultrasonic waves into electrical ultrasonic echo signals.

The ultrasonic echo signals are transmitted to the main body 100 via a wireless or wired communications network. Since the ultrasonic probe 110 receives the echo ultrasonic waves via a plurality of channels, the converted plurality of ultrasonic echo signals are transmitted to the main body 100 via the channels.

The transducers 111 of the ultrasonic probe 110 may be linear array transducers or convex array transducers. The ultrasonic probe 110 may be a two-dimensional (2D) array probe in which the transducers 111 are two-dimensionally arrayed.

Figure 5:
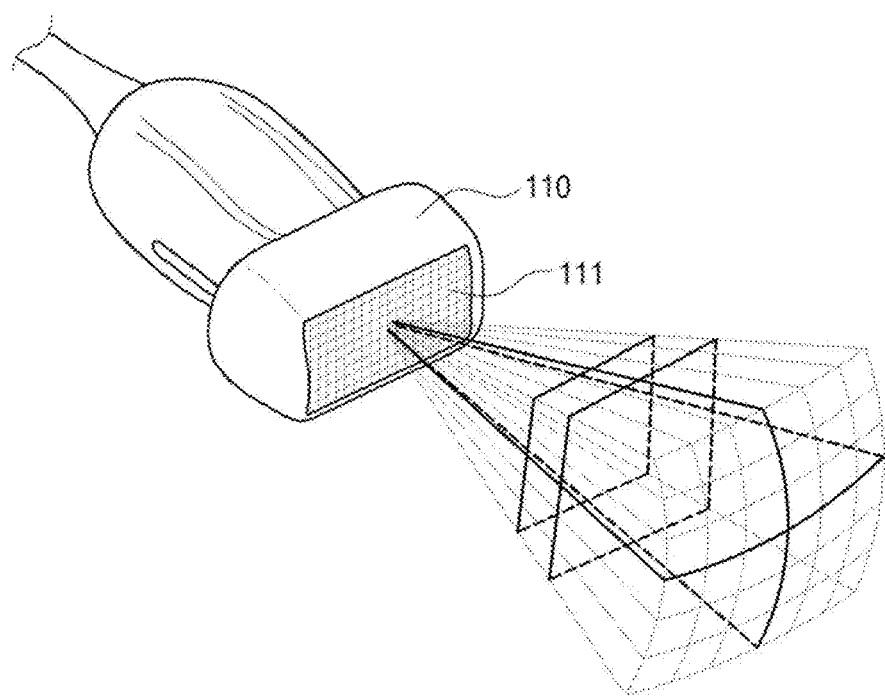
FIG. 5 is a diagram schematically illustrating emission of ultrasonic pulses to an object using a two-dimensional (2D) array probe.

FIG. 5 schematically illustrates a process of emitting ultrasonic pulses to the object using a two-dimensional (2D) array probe. The 2D array probe may include two-dimensionally arrayed transducers 111 while having a similar structure to a general ultrasonic probe. Thus, the plurality of transducers 111 is disposed on an XY plane. Hereinafter, the transducers 111 will be described based on locations thereof. For example, a column from the left of the X-axis and a row from the top of the Y-axis will be used to describe the transducers.

In FIG. 5, bold lines define available display planes. The 2D array probe may acquire 3D image information through electronic irradiation based on driving time delay of the transducers 111. Particularly, a tomogram, i.e., 2D data, of the object such as a plane defined by the bold lines is acquired. The 2D data is collected through the overall surface of the object by another group of transducers 111 differently arrayed. The collected 2D data are accumulated to generate a 3D image in real time. In addition, since a small-scale ultrasonic probe 110 may emit ultrasonic waves in a wide range, internal organs such as the heart may be efficiently irradiated.

Figure 6:
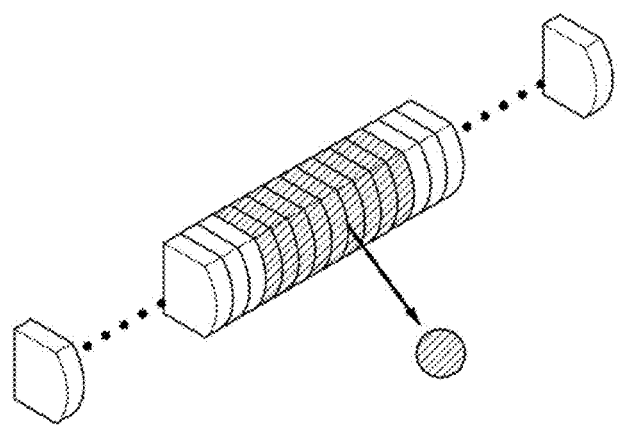
FIG. 6 is a diagram illustrating a process of emitting ultrasonic pulses to an object by an ultrasonic probe including one-dimensionally aligned transducers.

FIG. 6 is a diagram illustrating a process of emitting ultrasonic pulses to an object by an ultrasonic probe including one-dimensionally aligned transducers. When a plurality of transducers 111 is one-dimensionally aligned in a linear or convex array, the emission direction of ultrasonic pulses generated by the ultrasonic probe 110 has a 2D vector form. That is, since the transducers 111 are aligned in a row, there may be limitation to differently drive the transducers 111 in order to change the emission direction of the ultrasonic pulses.

Figure 7A:
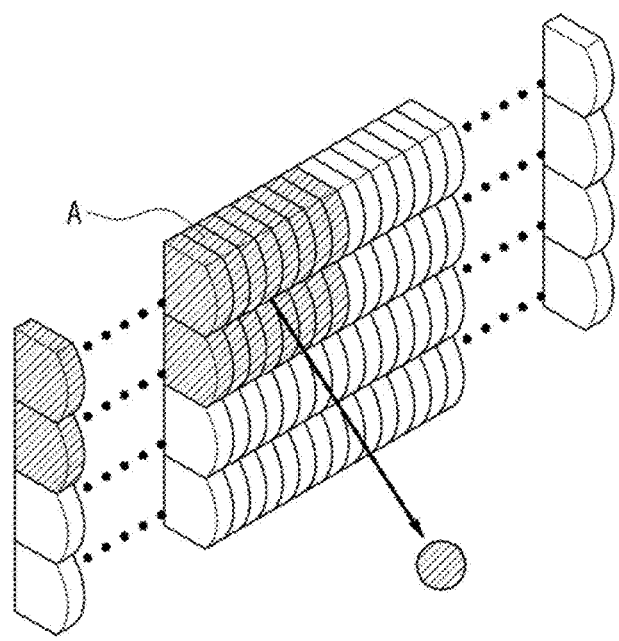
FIGS. 7A and 7B are diagrams illustrating a process of emitting ultrasonic pulses to an object by an ultrasonic probe including two-dimensionally arrayed transducers.
Figure 7B:
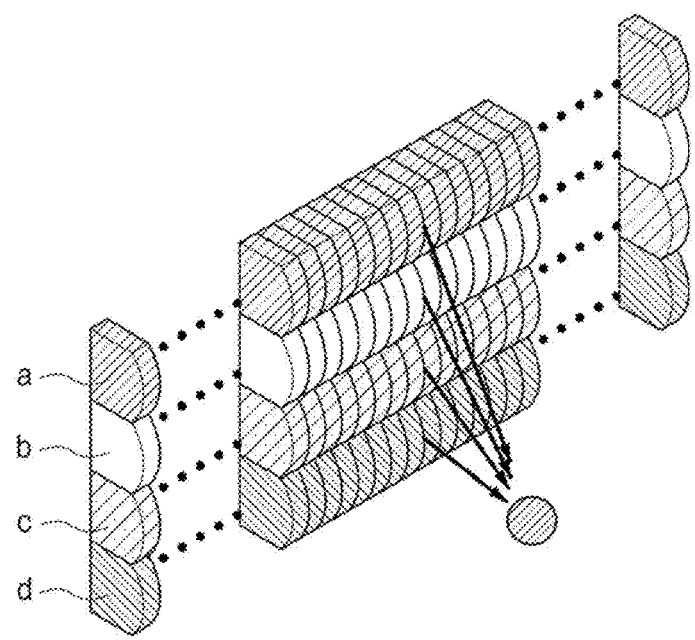
Figure 8:
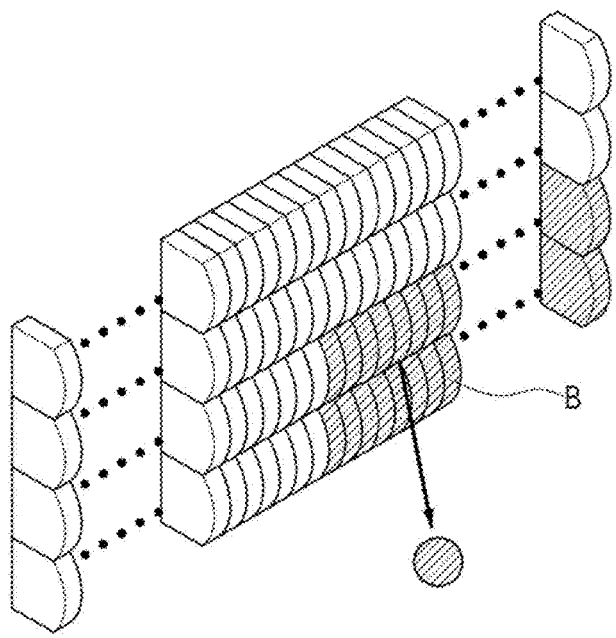
FIG. 8 is a diagram illustrating an ultrasonic probe including two-dimensionally arrayed transducers.

FIGS. 7A, 7B, and 8 are diagrams illustrating a process of emitting ultrasonic pulses to an object by an ultrasonic probe including two-dimensionally arrayed transducers. As an example of generating ultrasonic pulses having different proceeding directions, a 2D array probe may be used. According to an exemplary embodiment, the plurality of two-dimensionally arrayed transducers 111 may be divided into a plurality of regions. FIG. 7A illustrates that an ultrasonic pulse is emitted from a region A of the transducers 111 to the object. FIG. 8 illustrates that an ultrasonic pulse is emitted from a region B of the transducers 111 to the object. Arrows from the transducers 111 toward the object indicate emission directions of the ultrasonic pulse.

As described above, even in the same ultrasonic probe 110, emission directions of ultrasonic pulses from the transducers 111 located at different positions may be expressed as 3D vectors, and the 3D vectors may have different orientations. That is, the plurality of transducers 111 is divided into a plurality of regions, and the regions are independently driven, so that ultrasonic pulses may be emitted in different directions. By use of such characteristics, distortion caused as the location of the ultrasonic probe 110 changes may be efficiently corrected.

In this regard, the dividing of the transducers 111 into a plurality of regions may be directly input by a user via the input unit 150 or may be arbitrarily set via internal calculation. Since the normal vectors of the surface of the object need to be calculated by acquiring a plurality of ultrasonic echo signals corresponding to the ultrasonic pulses with different emission directions, the divided regions may be set without limitation.

FIG. 7B is a diagram illustrating an ultrasonic probe including two-dimensionally arrayed transducers divided according to rows. Hereinafter, the present exemplary embodiment will be described based on the divided transducers 111 by defining a first row as region a, defining a second row as region b, defining a third row as region c, and defining a fourth row as region d.

The plurality of transducers 111 may be divided into regions a, b, c, and d according to an exemplary embodiment. Arrows indicate emission directions of ultrasonic pulses respectively generated by respective transducers 111 of the regions a, b, c, and d toward the object. Upon comparison of the arrows illustrated in FIG. 7B, the emission directions of the ultrasonic pulses respectively generated in the transducers 111 of the regions are different. Here, the ultrasonic pulses are emitted in four different directions, and thus ultrasonic echo signals are also acquired in four different directions. When the transducers 111 are grouped as described above, the same effect as four one-dimensional (1D) array probes emitting ultrasonic pulses toward the object in different directions may be obtained.

As described above, even when the ultrasonic probe 110 having a 2D array is used, the generated ultrasonic pulses may be emitted in different directions, i.e., may have different 3D vectors, according to locations of the transducers 111. Thus, the generated ultrasonic pulses may be emitted in a plurality of directions. Accordingly, when a plurality of ultrasonic pulses is emitted to the same object in different directions through the 2D array probe and a plurality of ultrasonic echo signals are received, ultrasonic echo signals similar to the actual reflected ultrasonic echo signals may be acquired through calculation.

According to an exemplary embodiment of the ultrasonic image processing apparatus and a method thereof, a 2D array probe may be used to generate ultrasonic pulses having different emission directions. Hereinafter, an exemplary embodiment will be described on the assumption that the ultrasonic probe 110 is a 2D array probe.

Referring back to FIG. 2, the ultrasonic probe 110 may generate a plurality of ultrasonic pulses having different emission directions and may emit the ultrasonic pulses toward the object. In addition, the ultrasonic probe 110 may receive a plurality of echo ultrasonic waves reflected from the object. These processes need to be sequentially performed. Since echo ultrasonic waves reflected from ultrasonic pulses emitted in one direction may interfere with echo ultrasonic waves of ultrasonic pulses emitted in another direction, the echo ultrasonic waves acquired from the different directions might not be distinguished from each other. Thus, when the ultrasonic pulses are emitted in a first direction, the ultrasonic pulses need to be emitted in a second direction after the echo ultrasonic waves from the first direction are received.

The ultrasonic probe 110 may emit ultrasonic pulses in different directions, three or more directions, from divided regions including the transducers 111. In a calculation to obtain a normal vector of the surface of the object, which will be described later, components of the normal vector may be expressed as a 3D vector with x, y, and z coordinates. That is, when the ultrasonic pulses are emitted in three directions, three types of ultrasonic echo signals respectively having different intensities are acquired, and each component may be obtained through calculation of the matrix. This will be described in detail later with reference to the attenuation rate obtainer 101.

According to an exemplary embodiment, the main body 100 may include the attenuation rate obtainer 101, the corrector 102, and the beamformer 103. The main body 100 may be dispensed with some of the aforementioned constituent elements.

Referring to FIG. 2, the attenuation rate obtainer 101 may acquire ultrasonic echo signals, which are electrical signals converted from the echo ultrasonic waves, from the ultrasonic probe 110. Using the acquired ultrasonic echo signals, the amount of loss from the ultrasonic echo signals actually reflected from the object according to the proceeding direction, i.e., an attenuation rate of the received ultrasonic echo signals to the actual reflected ultrasonic echo signals may be calculated. The ultrasonic probe 110 receives only some of the ultrasonic echo signals actually reflected from the object. The attenuation rate of the actual reflected ultrasonic echo signals may be used when the corrector 102 corrects the received ultrasonic echo signals into the actual reflected ultrasonic echo signals, which will be described later.

A complex function may be used to calculate the ratio of the received echo ultrasonic waves to the actual reflected echo ultrasonic waves. Thus, a Lambertian surface model may be used to simplify the calculation.

The Lambertian surface model refers to a reflector with a constant speed of light in all directions at a solid angle indicating an object having a uniform intensity of reflection regardless of angle of view. According to the Lambertian surface model, intensity of reflected light is proportional to the cosine of an angle between the normal vector of the surface of the object and the emission direction of the light toward the object. This may be represented by Equation 2.

$$I = I_E \times \cos\theta \qquad \text{[Equation 2]}$$

When Equation 2 is applied to the ultrasonic image processing apparatus and the method thereof, I indicates an ultrasonic echo signal received from the ultrasonic probe 110, $I_E$ indicates an actual reflected ultrasonic echo signal, and θ indicates an angle between an emission direction of the ultrasonic pulse emitted toward the object and the normal vector of the surface of the object. Thus, the ratio of the received ultrasonic echo signal to the actual reflected ultrasonic echo signal, i.e., attenuation rate of the reflected ultrasonic echo signal, is cos θ. Ultimately, correcting the ultrasonic echo signal acquired by emitting the ultrasonic pulse entails substituting the actual reflected ultrasonic echo signal for the acquired ultrasonic echo signal.

Thus, the normal vector of the surface of the object needs to be obtained before calculating θ. To calculate the normal vector of the surface of the object, a plurality of ultrasonic pulses to be emitted in different directions is generated while fixing the position of the ultrasonic probe 110. The ultrasonic probe 110 emits the generated ultrasonic pulses to the object so as to receive echo ultrasonic waves respectively corresponding to the ultrasonic pulses. The received echo ultrasonic waves are substituted into Equation 2 in a matrix form to calculate the normal vector of the surface of the object. The normal vector of the surface of the object is calculated using Equation 1 below.

$$I_E \times \vec{N} = \begin{pmatrix} \vec{L_1} \\ \vec{L_2} \\ \vec{L_3} \end{pmatrix} \cdot \begin{pmatrix} I_1 \\ I_2 \\ I_3 \end{pmatrix}$$ [Equation 1]

When Equation 1 is applied to the ultrasonic image processing apparatus and the method thereof, $I_E$ indicates an actual reflected ultrasonic echo signal, and $\vec{N}$ indicates a normal vector of the surface of the object. In addition, $\vec{L_1}$, $\vec{L_2}$, and $\vec{L_3}$ are unit direction vectors in the emission direction of the ultrasonic pulses emitted from the ultrasonic probe 110 toward the object. $I_1$, $I_2$, and $I_3$ indicate ultrasonic echo signals acquired by emitting the ultrasonic pulses.

Equation 1 is rewritten in terms of the normal vector $\vec{N}$ of the surface of the object, each component of the normal vector $\vec{N}$ is a function of an ideal ultrasonic echo signal $I_E$. In addition, using the normal vector $\vec{N}$ and the unit direction vectors $\vec{L_1}$, $\vec{L_2}$, and $\vec{L_3}$ in the emission direction of the ultrasonic pulse emitted from the ultrasonic probe 110 toward the object, each having a magnitude of 1, the components of the normal vector $\vec{N}$ may be calculated.

Three direction vectors of the ultrasonic pulses emitted from the ultrasonic probe 110 to the object and three ultrasonic echo signals acquired by use of the ultrasonic pulses are needed in Equation 1. This is because Equation 1 has three unknowns, i.e., x, y, and z components of the normal vector $\vec{N}$ of the surface of the object. Thus, three equations with the components of the normal vector $\vec{N}$ of the surface of the object are needed. To this end, three direction vectors of the ultrasonic pulses emitted from the ultrasonic probe 110 to the object and three ultrasonic echo signals acquired by use of the ultrasonic pulses are substituted into Equation 1.

However, the ultrasonic probe 110 may generate direction vectors of the ultrasonic pulses having four or more directions and emit the ultrasonic pulses. In this case, since three direction vectors of the ultrasonic pulses and three ultrasonic echo signals acquired by use of the ultrasonic pulses are needed in Equation 1, three direction vectors and three ultrasonic echo signals may be respectively selected from four or more thereof.

Alternatively, the four or more direction vectors and ultrasonic echo signals are respectively classified into several groups and averages of the groups calculated therefrom may be substituted into Equation 1. By use of the averages, distortion of an ultrasonic image caused by noise may be prevented.

In order to calculate the averages of direction vectors and ultrasonic echo signals, various algorithms may be used. Particularly, a least mean squares algorithm may be applied to an ultrasonic image processing apparatus for processing a large amount of data while having a small calculation amount. According to the least mean squares algorithm, an ultrasonic image may be processed in real time based on high calculation rate. The least mean squares algorithm is well known in the art, and thus a detailed description thereof will not be given.

By use of the normal vector $\vec{N}$ of the surface of the object, the angle θ between the normal vector of the surface of the object and the emission direction of the ultrasonic pulse emitted from the ultrasonic probe 110 to the object may be calculated. Thus, cos θ acquired by substituting the calculated angle into the cosine function indicates the attenuation rate of the actual reflected ultrasonic echo signal. Accordingly, the ratio of the received ultrasonic echo signal to the reflected ultrasonic echo signal may be determined.

Referring back to FIG. 2, the corrector 102 receives the attenuation rate of the actual reflected ultrasonic echo signals acquired by the attenuation rate obtainer 101. The actual reflected ultrasonic echo signals are acquired based on the attenuation rate of the received ultrasonic echo signals. The corrected ultrasonic echo signals, i.e., the reflected ultrasonic echo signals, are calculated using Equation 2 described above.

The corrected ultrasonic echo signals are values from which virtual light source effect caused by the position of the ultrasonic probe 110 is removed. Thus, the correction process contributes to output an ultrasonic image with greater realism than a process of converting the corrected ultrasonic echo signals into ultrasonic image signals performed by the beamformer 103.

The beamformer 103 performs beamforming based on the ultrasonic echo signals corrected by the corrector 102. Beamforming is a process of focusing the ultrasonic echo signals input via a plurality of channels and acquiring appropriate ultrasonic image signals with respect to the inside of the object.

The beamformer 103 compensates for time difference of ultrasonic echo signals caused distance difference between each of the transducers 111 and the target region in the object. Then, the beamformer 103 may emphasize ultrasonic echo signals from one of the channels and relatively attenuate ultrasonic echo signals from the other channels so as to focus the ultrasonic echo signals. In this case, the beamformer 103 may emphasize or attenuate ultrasonic echo signals from a particular channel by weighting the ultrasonic echo signals input via each channel.

The beamformer 103 may focus the ultrasonic echo signals acquired by the ultrasonic probe 110 at each of a plurality of frames in consideration of the locations of the transducers 111 of the ultrasonic probe 110 and a focus point.

Meanwhile, the beamforming performed by the beamformer 103 may include data-independent beamforming and adaptive beamforming.

The display outputs the ultrasonic image signals converted by the beamformer 103 on a screen. The display includes a main display and a sub-display and displays data regarding the object on the screen as an image for ultrasonic diagnosis.

Figure 9:
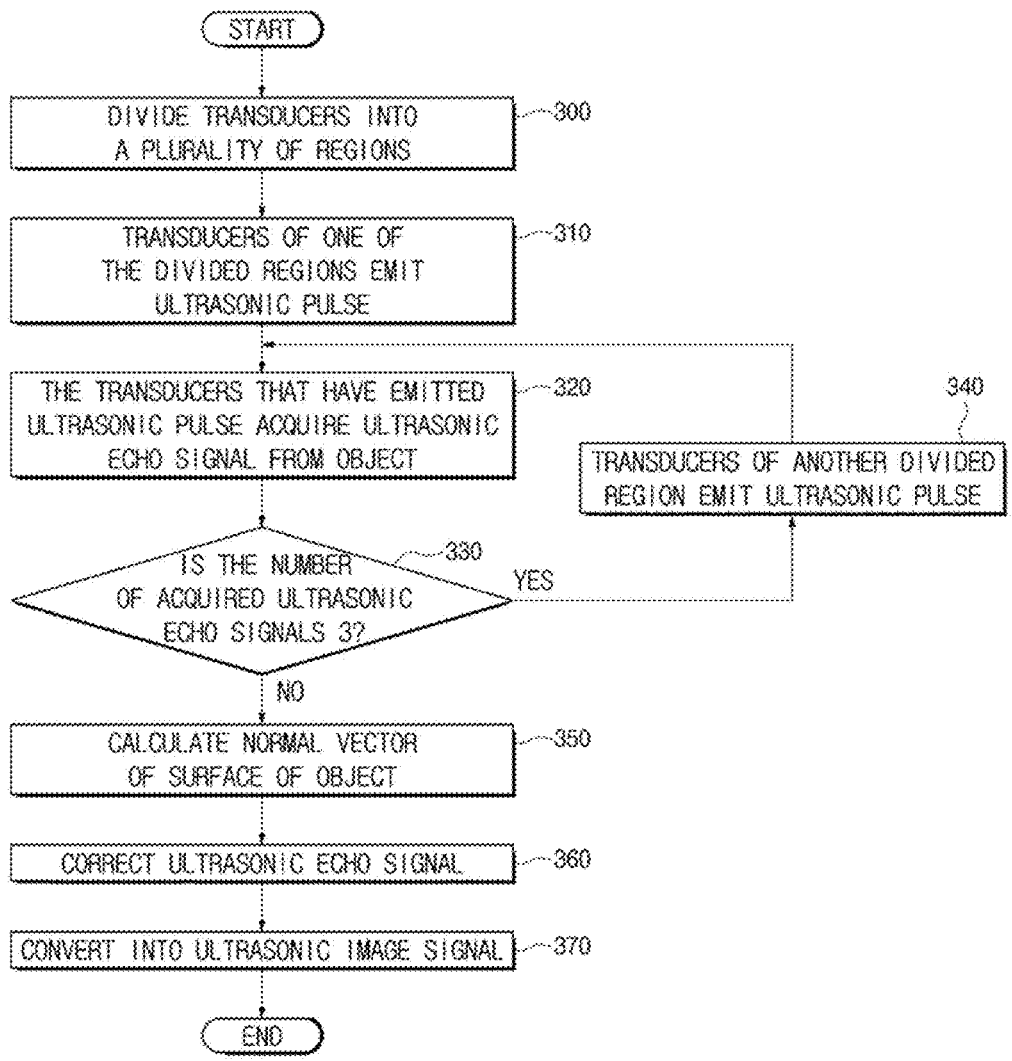
FIG. 9 is a flowchart illustrating a method of processing an ultrasonic image including acquiring ultrasonic echo signals.

FIG. 9 is a flowchart illustrating a method of processing an ultrasonic image including acquiring ultrasonic echo signals.

A plurality of transducers 111 of the ultrasonic probe 110 is divided into a plurality of regions (operation 300). Here, the ultrasonic probe 110 is a 2D array probe. A proceeding direction of an ultrasonic pulse is expressed as a 2D vector in the transducer 111 of the 1D array probe. On the other hand, when the transducers 111 of the 2D array probe are divided into the plurality of regions, an ultrasonic pulse expressed as a 3D vector may be emitted to the same object from each region of the divided transducers 111. Components of a 3D vector, which are expressed as x, y, and z coordinates, may be efficiently substituted into Equation 1.

A process of emitting ultrasonic pulses in different directions and a process of acquiring a plurality of ultrasonic echo signals need to be sequentially performed. Thus, ultrasonic pulses are emitted from one of the divided regions of the transducers 111 (operation 310). Then, ultrasonic echo signals reflected from the emitted ultrasonic pulses are acquired (operation 320). The emission of the ultrasonic pulses and acquisition of the ultrasonic echo signals are performed in the same region of the transducers 111.

A next stage is performed after comparing the number of acquired ultrasonic echo signals (operation 330). Since a normal vector of the surface of the object will be obtained to correct the ultrasonic echo signals by use of Equation 1 in the next stage, three emission directions of the ultrasonic pulses and three acquired ultrasonic echo signals are needed.

When, the number of the acquired ultrasonic echo signals is less than 3, ultrasonic pulses are emitted from another region, different from the previous region, of the divided transducers 111 toward the object (operation 340). Accordingly, ultrasonic echo signals are additionally acquired. However, when the number of the acquired ultrasonic echo signals is less than 3, a next stage will be performed.

When it is confirmed that three ultrasonic echo signals are acquired, these values are substituted into Equation 1 so as to obtain the normal vector of the surface of the object (operation 350). Specific values of each component of the normal vector are acquired by simplifying each component of the normal vector according to Equation 1 and using the fact that the sizes of the normal vector and the unit direction vectors in the emission direction of the ultrasonic pulses are 1.

By use of the acquired normal vector, the acquired ultrasonic echo signals are corrected to be similar to the actual reflected ultrasonic echo signals (operation 360). Particularly, an angle between the normal vector of the surface of the object and the emission direction of the ultrasonic pulse emitted toward the object is obtained. The obtained angle is substituted into the cosine function to calculate the attenuation rate of the actual reflected ultrasonic echo signals. Finally, the attenuation rate is substituted into Equation 2 to calculate the ultrasonic echo signals actually reflected from the object. The actual reflected ultrasonic echo signals are corrected ultrasonic echo signals.

After the ultrasonic echo signals are appropriately corrected, the beamformer 103 converts the corrected ultrasonic echo signals into ultrasonic image signals (operation 370). The converted ultrasonic image signals are signals from which the virtual light source effect in a direction from the ultrasonic probe 110 is removed. Thus, an image with high realism may be generated.

FIG. 10 is a flowchart illustrating a method of processing an ultrasonic image when four or more ultrasonic echo signals are acquired.

A plurality of transducers 111 of a 2D array probe is divided into a plurality of regions, and ultrasonic pulses may be respectively emitted from the regions. Emitting the ultrasonic pulses from different regions of the transducers 111 indicates that the ultrasonic pulses are emitted in different directions. A plurality of ultrasonic echo signals corresponding to the emission directions changed as described above is acquired (operation 400).

Upon comparison of the number of acquired ultrasonic echo signals as described above, it is determined whether the process enters into a next stage. That is, when the number of the acquired ultrasonic echo signals is less than N, the aforementioned process is repeated in order to additionally acquire the ultrasonic echo signals (operation 400). However, when the number of the acquired ultrasonic echo signals is N or greater, the process enters the next stage.

Here, N is a natural number of 4 or more. It has been described above that three values are needed to calculate the 3D normal vector of the surface of the object. In addition, when four or more ultrasonic echo signals are acquired, three values need to be selected or averages need to be calculated. Hereinafter, a method of correcting the ultrasonic echo signals using averages of four or more ultrasonic echo signals will be described.

N may be input by the user via the input unit 150 or may be selected via calculation of the apparatus.

When the number of the acquired ultrasonic echo signals is N or greater, an average thereof is calculated to remove noise (operation 420). Since three equations may be derived from Equation 1, three unit direction vectors in the emission direction of the ultrasonic pulses and three ultrasonic echo signals may be respectively substituted thereinto. Thus, by reducing four or more data into three values by averaging, data close to the real values may be substituted into Equation 1.

Thus, averages of the acquired ultrasonic echo signals and the direction vectors in the emission direction of the ultrasonic pulse are calculated. For example, the averages may be calculated using a least mean squares algorithm. The least mean squares algorithm is well known in the art, and thus a detailed description thereof will not be given.

The averages of the acquired ultrasonic echo signals and the direction vectors in the emission direction of the ultrasonic pulse are substituted into Equation 2 so as to calculate a normal vector of the surface of the object (operation 430). Three averages of the ultrasonic echo signals acquired according to the ultrasonic image processing apparatus and the method thereof may be substituted thereinto, or one average and two measured values may be substituted thereinto.

The ultrasonic echo signals are corrected using the normal vector of the surface of the object (operation 440). When the angle between the normal vector and the emission direction of the ultrasonic pulse is calculated and substituted into the cosine function, the attenuation rate of the actual reflected ultrasonic echo signals may be obtained. Thus, the ultrasonic echo signals are corrected by calculating the actual reflected ultrasonic echo signals based thereon and replacing the acquired ultrasonic echo signals with the actual reflected ultrasonic echo signals.

The corrected ultrasonic echo signals are converted into ultrasonic image signals by the beamformer 103 (operation 450). When the converted ultrasonic image signals are output to the screen through the display, a user may confirm an ultrasonic image from which the effect, in which a virtual light source is located in a direction from the ultrasonic probe 110, is removed. Thus, an ultrasonic image of the object with high realism may be output through the correction process.

According to the ultrasonic image processing apparatus and the method thereof, errors caused by reflectivity difference in accordance with the position of the probe may be reduced. Accordingly, a density closer to the intrinsic density of the medium may be acquired using the same. As a result, accuracy may be increased in ultrasonic diagnosis.

This may be efficiently applied to an ultrasonic image output when the object is viewed in a particular direction or 3D ultrasonic diagnosis through which cross-sections of the object are reorganized and observed.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasonic imaging method comprising:
    sequentially emitting by each transducer group of respective regions, into which a plurality of transducers of an ultrasonic probe are divided, focused ultrasonic pulses to a same focal point of an object in a first sequential manner;
    sequentially acquiring, by each transducer group, ultrasonic echo signals reflected from the same focal point of the object in correspondence to the sequentially emitted ultrasonic pulses, in a second sequential manner;
    calculating, via a processor of an ultrasound apparatus, a normal vector of a surface of the object using emission directions of the focused ultrasonic pulses emitted by at least three of the transducer groups and intensities of the acquired ultrasonic echo signals in correspondence to the focused ultrasonic pulses emitted by the at least three of the transducer groups;
    calculating, via the processor, an attenuation rate of the acquired ultrasonic echo signals using the calculated normal vector and emission directions of the focused ultrasonic pulses emitted by the at least three of the transducer groups, and correcting the acquired ultrasonic echo signals based on the attenuation rate;
    beamforming the ultrasonic echo signals, an attenuation of which has been corrected, into ultrasonic image signals; and
    outputting, on a display, the ultrasonic image signals as an ultrasonic image,
    wherein the attenuation rate is directly proportional to the intensity of the acquired ultrasonic echo signals, and is independent of a depth of focus.

2. The method according to claim 1, wherein the ultrasonic probe comprises a two-dimensional (2D) array probe.

3. The method according to claim 2, wherein the plurality of transducers are divided into the regions so that transducers of the plurality of transducers, disposed in a same row belong to a same transducer group.

4. The method according to claim 2, wherein the plurality of transducers are divided into three or more regions to emit the ultrasonic pulses in three or more emission directions.

5. The method according to claim 4, wherein the attenuation rate is a cosine of an angle between the normal vector of the surface of the object and an emission direction vector of the ultrasonic pulses.

6. The method according to claim 5, wherein the ultrasonic pulses are emitted in four or more directions, and
    the calculating the normal vector of the surface of the object comprises calculating the normal vector of the surface of the object by using averages of emission direction vectors of the ultrasonic pulses and averages of the acquired ultrasonic echo signals.

7. The method according to claim 6, wherein the correcting the acquired ultrasonic echo signals is performed using Equation 2:

$$I = I_E \times \cos \theta \quad \text{[Equation 2]}$$

wherein I is the intensity of the acquired ultrasonic echo signal, $I_E$ is the intensity of actual reflected ultrasonic echo signal, and $\theta$ is an angle between the ultrasonic pulse and the normal vector of the surface of the object.

8. An ultrasonic image processing apparatus comprising:
    an ultrasonic probe comprising a plurality of transducers which are divided into regions for forming transducer groups, each of the transducer groups being configured to sequentially emit focused ultrasonic pulses to a same focal point of an object in a first sequential manner and sequentially acquire echo signals reflected from the same focal point of the object in a second sequential manner;
    a processor configured to calculate a normal vector of a surface of the object using emission directions of the focused ultrasonic pulses emitted by at least three of the transducer groups and intensities of the acquired ultrasonic echo signals in correspondence to the focused ultrasonic pulses emitted by the at least three of the transducer groups, calculate an attenuation rate of the acquired ultrasonic echo signals using the calculated normal vector and emission directions of the focused ultrasonic pulses emitted by the at least three of the transducer groups, and correct the acquired ultrasonic echo signals based on the attenuation rate;
    a beamformer configured to convert the ultrasonic echo signals, an attenuation of which have been corrected, into ultrasonic image signals; and
    a display configured to output the ultrasonic image signals as an image,
    wherein the attenuation rate is directly proportional to the intensity of the acquired ultrasonic echo signals, and is independent of a depth of focus.

9. The ultrasonic image processing apparatus according to claim 8, wherein the plurality of transducers of the ultrasonic probe comprises two-dimensionally arrayed transducers.

10. The ultrasonic image processing apparatus according to claim 9, wherein the two-dimensionally arrayed transducers are divided into the regions so that transducers of the plurality of transducers, disposed in a same row belong to a same transducer group.

11. The ultrasonic image processing apparatus according to claim 9, wherein the plurality of transducers are divided into three or more regions to emit the ultrasonic pulses in three or more emission directions.

12. The ultrasonic image processing apparatus according to claim 11, wherein the attenuation rate is a cosine of an angle between the normal vector of the surface of the object and an emission direction vector of the ultrasonic pulses.

13. The ultrasonic image processing apparatus according to claim 12, wherein the ultrasonic pulses are emitted in four or more directions, and
    the processor is further configured to calculate the normal vector of the surface of the object using averages of emission direction vectors of the ultrasonic pulses and averages of the acquired ultrasonic echo signals.

14. The ultrasonic image processing apparatus according to claim 13, wherein the processor is configured to correct the acquired ultrasonic echo signals using Equation 2:

$$I = I_E \times \cos \theta \quad \text{[Equation 2]}$$

wherein I is the intensity of the acquired ultrasonic echo signal, $I_E$ is the intensity of the actual reflected ultrasonic echo signal, and θ is an angle between the ultrasonic pulse and the normal vector of the surface of the object.

* * * * *